United States Patent [19]

Sirhan et al.

[11] Patent Number: 5,709,658
[45] Date of Patent: Jan. 20, 1998

[54] RAPID EXCHANGE TYPE OVER-THE-WIRE CATHETER

[75] Inventors: Motasim M. Sirhan; Robert F. Kotmel, both of Sunnyvale; Susan M. Feltovich, Santa Clara, all of Calif.

[73] Assignee: Advanced Cardiovascular Systems, Inc., Santa Clara, Calif.

[21] Appl. No.: 602,681

[22] Filed: Feb. 16, 1996

Related U.S. Application Data

[63] Continuation of Ser. No. 432,213, May 1, 1995, abandoned, which is a continuation of Ser. No. 88,842, Jul. 8, 1993, Pat. No. 5,413,559.

[51] Int. Cl.$^6$ .................................................. A61M 29/00
[52] U.S. Cl. .................... 604/102; 604/160; 604/283; 604/284
[58] Field of Search ........................ 604/96–103, 160, 604/283, 284, 905; 606/192–6; 600/18

[56] References Cited

U.S. PATENT DOCUMENTS

| | | | |
|---|---|---|---|
| 4,981,478 | 1/1991 | Evard et al. | 604/282 |
| 4,988,356 | 1/1991 | Crittenden et al. | 606/192 |
| 5,045,061 | 9/1991 | Seifert et al. | 604/96 |
| 5,135,535 | 8/1992 | Kramer | 606/194 |
| 5,154,725 | 10/1992 | Leopold | 606/194 |
| 5,171,222 | 12/1992 | Euteneuer et al. | 604/102 |
| 5,217,482 | 6/1993 | Keith | 606/194 |
| 5,219,332 | 6/1993 | Nelson et al. | 604/95 |
| 5,263,932 | 11/1993 | Jang | 604/96 |
| 5,273,533 | 12/1993 | Bonaldo | 604/86 |
| 5,292,305 | 3/1994 | Boudewijn et al. | 604/283 |
| 5,338,299 | 8/1994 | Barlow | 604/96 |
| 5,413,559 | 5/1995 | Sirhan et al. | 604/283 |
| 5,487,729 | 1/1996 | Avellanet et al. | 604/283 |

*Primary Examiner*—Michael Powell Buiz
*Assistant Examiner*—Bhisma Mehta
*Attorney, Agent, or Firm*—Heller, Ehrman, White & McAuliffe

[57] ABSTRACT

An intraluminal catheter, particularly a dilatation catheter for PTCA procedures, which is adapted for rapid exchange during an intraluminal procedure and which also allows for the exchange of the guidewire without loss of access to the intraluminal region about the distal end of the catheter. The catheter has a main guidewire lumen which extends essentially the length of the catheter and a guidewire extension lumen which extends proximally from the main guidewire lumen and is at least in part offset and parallel to the main guidewire lumen. A portion of the catheter shaft which defines at least part of the main guidewire lumen has a first slit from the proximal end of the catheter to the intersection between the extension lumen and the main guidewire lumen and a second lumen which extends from a proximal guidewire port in the guidewire extension lumen to a port in the distal end of the catheter. Also disclosed is an adapter having a slit which is continuous with the slit in the proximal extremity of the catheter shaft which facilitates separation of the guidewire and the catheter when the adapter is fixed to the proximal end of the catheter shaft.

5 Claims, 3 Drawing Sheets

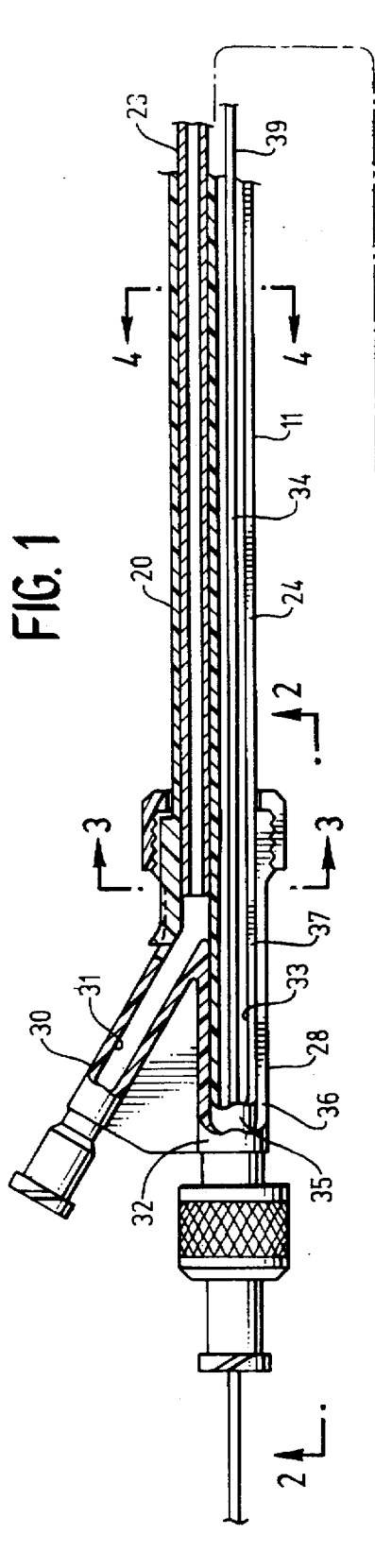
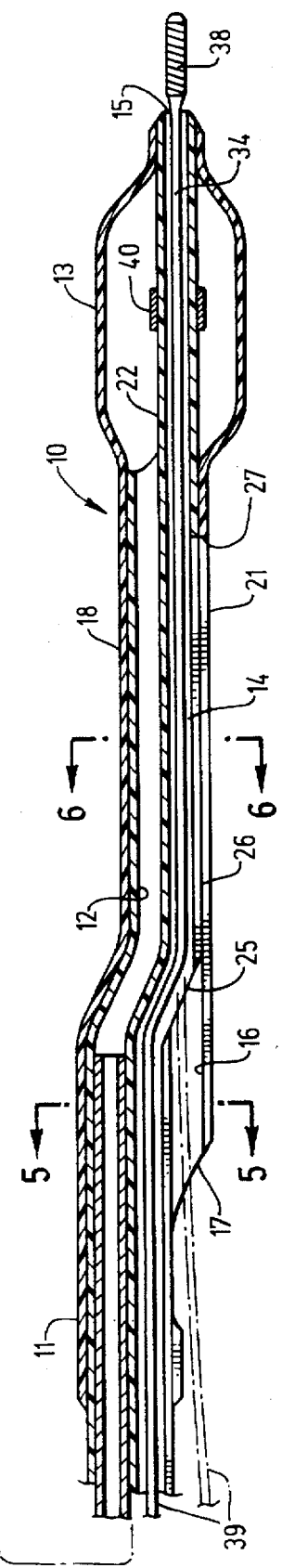
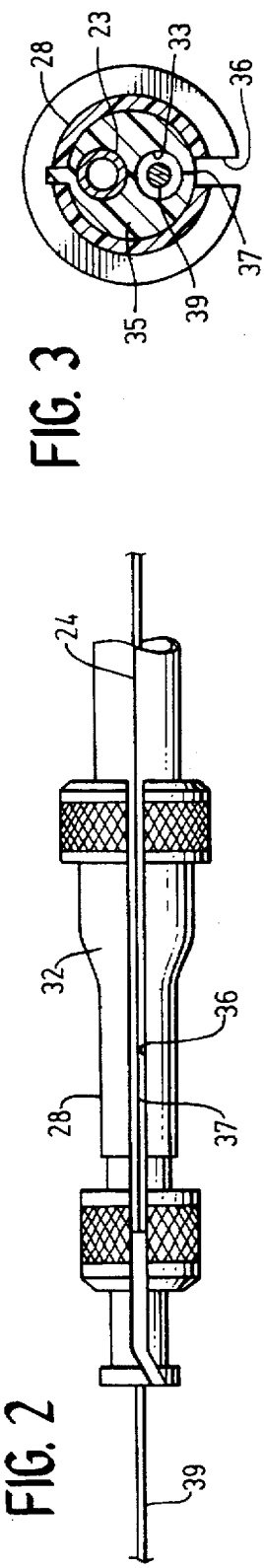
FIG. 1
FIG. 2
FIG. 3

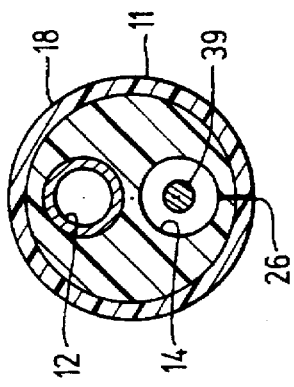
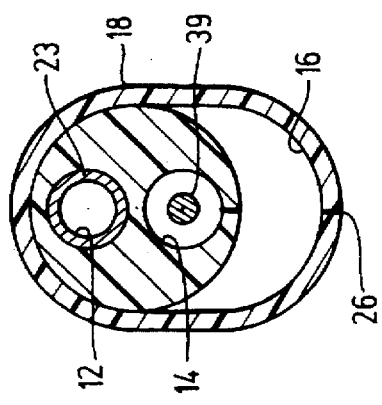
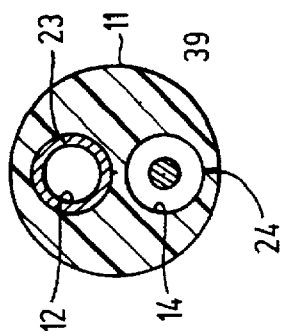
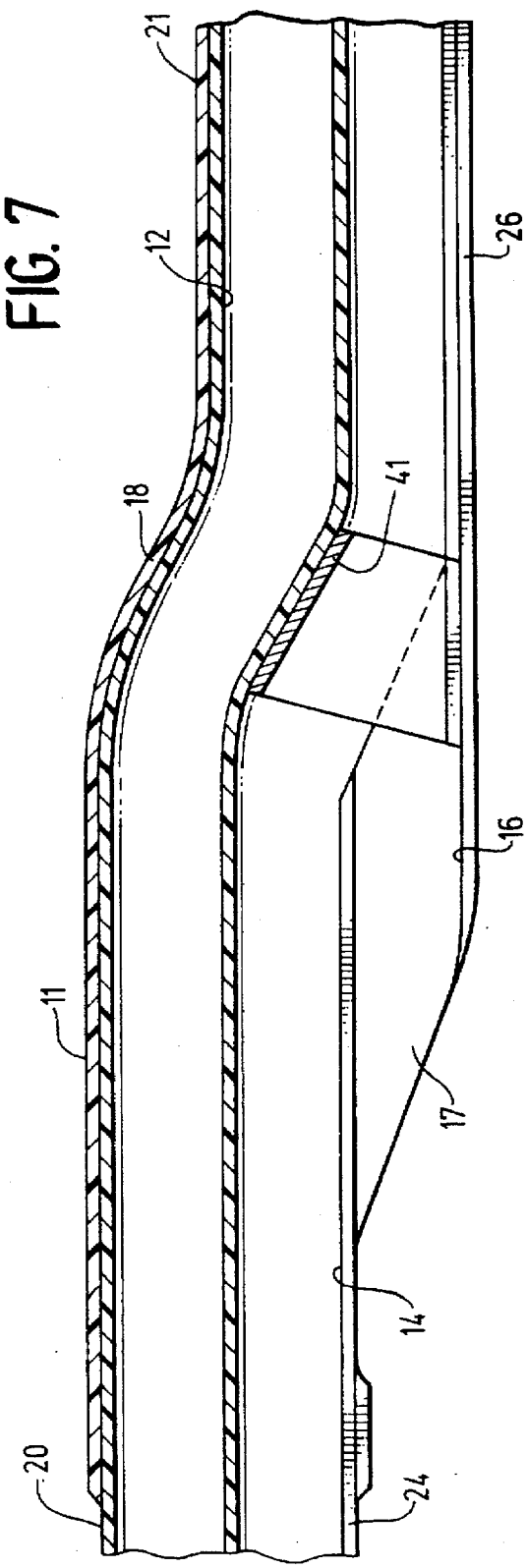

RAPID EXCHANGE TYPE OVER-THE-WIRE CATHETER

This is a continuation of application Ser. No. 08/432,213 now abandoned which was filed on May 1, 1995 which is a continuation of application Ser. No. 08/088,842, filed Jul. 8, 1993, now U.S. Pat. No. 5,413,559.

BACKGROUND OF THE INVENTION

This invention generally relates to a rapid exchange type dilatation catheter system which is suitable for intravascular procedures such as percutaneous transluminal coronary angioplasty (PTCA) and which allows for the exchange of the guidewire during such procedures without loss of access to the patient's arterial location.

In PTCA procedures, a guiding catheter having a preshaped distal tip is percutaneously introduced into the cardiovascular system of a patient and advanced therein until the preshaped distal tip thereof is disposed within the aorta adjacent to the ostium of the desired coronary artery. The guiding catheter is twisted or torqued from the proximal end to turn the distal tip of the guiding catheter so that it can be guided into the coronary ostium. A dilatation catheter having a balloon on the distal end thereof and a guidewire slidably disposed within an inner lumen of the thereof and a guidewire slidably disposed within an inner lumen of the dilatation catheter are introduced into and advanced through the guiding catheter to the distal tip thereof. The distal tip of the guidewire is usually manually shaped (i.e. curved) by the physician or one of the attendants before the guidewire is introduced into the guiding catheter along with the dilatation catheter. The guidewire is first advanced out the distal tip of the guiding catheter, which is seated in the ostium of the patient's coronary artery, into the patient's coronary artery. A torque is applied to the proximal end of the guidewire, which extends out of the patient, to guide the curved or otherwise shaped distal end of the guidewire as the guidewire is advanced within the coronary anatomy until the shaped distal end of the guidewire enters the desired artery. The advancement of the guidewire within the selected artery continues until it crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the flexible, relatively inelastic balloon is inflated to a predetermined size with radiopaque liquid at relatively high pressures (e.g., 4–12 atmospheres) to dilate the stenosed region of the diseased artery. The balloon is then deflated so that the dilatation catheter can be removed from the dilated stenosis and blood flow can then be resumed therethrough.

A rapid exchange type dilatation catheter has a short guidewire-receiving sleeve or inner lumen extending a short distance through just the distal portion of the catheter shaft. The sleeve or inner lumen preferably extends proximally at least about 10 cm, typically about 25 cm, from a first guidewire port in the distal end of the catheter to a second guidewire port. A slit may be provided in the catheter wall defining the first guidewire receiving lumen which extends proximally from a location proximal to the inflatable balloon to the second guidewire port to facilitate the separation of the catheter from the guidewire. The catheter is advanced within the patient's vascular system with the guidewire disposed within the guidewire receiving inner lumen in the distal section of the catheter shaft in a conventional fashion. Alternatively, the guidewire may be first advanced within the patient's vasculature until the distal end of the guidewire extends distally to the stenosis to be dilated and then the catheter is mounted onto the proximal end of the in-place guidewire and then advanced over the guidewire until the dilatation balloon is properly disposed across the stenosis. The structure of the catheter allows for the rapid exchange of the catheter without the need for an exchange wire or adding a guidewire extension to the proximal end of the guidewire.

Rapid exchange type catheters are available from the licensee of the present invention, Advanced Cardiovascular Systems, Inc., under the trademark ACS RX® which are basically described and claimed in U.S. Pat. No. 5,061,273 (Yock) and U.S. Pat. No. 4,748,982 (Horzewski et al.). The catheter design embodying the Yock and Horzewski et al. improvements has been widely praised by members of the medical profession and it has met with much commercial success in the market place. Nonetheless, there are some inconveniences in its use because the catheter does not allow for the exchange or replacement of the guidewire. For example, the shaped distal tip of the guidewire may become deformed in use or the shape of the distal tip or the size of the guidewire may be found to be no longer suitable for the particular procedure within the patient's vasculature. In this instance the physician might want to remove the guidewire and reshape the distal tip or replace the first guidewire with another having the desired size, stiffness or shape. However, when the guidewire in a dilatation catheter system embodying the Yock and Horzewski et al. improvements is removed, access to the desired arterial location through the distal guidewire lumen of the catheter is lost. Unfortunately, there is no way to clinically determine before the guidewire is inserted into the patient in an angioplasty procedure whether a guidewire or a catheter will have to be exchanged during the procedure.

What has been needed and heretofore unavailable is an easily usable intravascular catheter system which allows for the rapid exchange of either the catheter or the guidewire during an intravascular procedure without losing access to the desired region of the patient's arterial system. The present invention satisfies this and other needs.

SUMMARY OF THE INVENTION

This invention is directed to a rapid exchange type dilatation catheter system which allows for the exchange of a guidewire, which can also be used as an over-the-wire type dilatation catheter without losing access to the location of the distal portion of the catheter within the patient's body lumen.

The catheter system of the invention generally comprises an elongated catheter shaft having proximal and distal ends, an inflation lumen extending from the proximal end of the catheter shaft to a location in a distal section of the catheter shaft and a main guidewire lumen extending from the proximal end of the catheter shaft to a guidewire port in the distal end of the catheter shaft and a guidewire lumen extension in the distal portion of the catheter shaft which is in communication with the main guidewire lumen and which extends proximally away from the main guidewire lumen to a proximal guidewire port offset from the main guidewire lumen. An inflatable member is provided on the distal section of the catheter shaft which is in fluid communication with the inflation lumen. The proximal guidewire port is spaced a short distance proximally, e.g. about 10 cm to usually not more than about 50 cm, from the distal guidewire port. The proximal guidewire port is a substantial distance from the proximal end of the catheter shaft.

A slit may be provided in a wall of the proximal section of the catheter shaft which defines at least in part the guidewire receiving lumen extending therein in order to facilitate the separation of the guidewire within the guidewire lumen and the catheter shaft. The slit extends through the wall to the location where the guidewire lumen extension in the distal section of the catheter shaft intersects the guidewire extension lumen. Preferably, at the junction between the proximal and distal shaft sections, a truncated conical support member is disposed within the intersection of the guidewire lumen extension and the guidewire lumen. The conical support member should be thin walled and is preferably made of a flexible, high strength material such as polyamide, superelastic NiTi alloys and the like.

An adapter is provided on the proximal end of the catheter shaft which is adapted to direct inflation fluid into the inflation lumen in the proximal section of the catheter shaft. The adapter is preferably a multi-arm adapter with a second arm for directing inflation fluid to the inflation lumen and a first arm having an inner lumen which is adapted to receive a guidewire therein and which is in communication with the main guidewire receiving lumen. In one presently preferred embodiment the first arm of the adapter has a slit continuous with the slit in the proximal section of the shaft to facilitate the separation therefrom of a guidewire disposed within fie inner lumen of the first arm when the guidewire is removed from the main guidewire receiving lumen in the proximal section of the catheter shaft. It is also preferred to provide a slit in the wall of the distal section of the catheter shaft which defines the main guidewire receiving lumen therein to facilitate the separation of the guidewire from the distal section of the catheter shaft. Generally, the slit will extend from the second guidewire port to a location proximal to the inflatable dilatation member on the distal catheter shaft section.

One of the attractive features of the rapid exchange type dilatation catheter of the invention is that it can be initially advanced within a patient's vascular system either in a rapid exchange mode with the guidewire extending through just the guidewire receiving lumen in the distal section of the catheter shaft or in a conventional over-the-wire mode with the guidewire extending through the main guidewire receiving lumen throughout essentially the entire length of the catheter shaft. In addition to exchanging the catheter, the catheter design also allows the guidewire to be exchanged during the PTCA procedure.

To replace the catheter of the invention during a PTCA procedure, the in-place catheter is pulled proximally over the guidewire by the proximal end of the catheter. If the catheter is being used in the rapid exchange mode, the catheter is withdrawn from the patient by peeling the dilatation catheter off of the guidewire through the slit extending distally from the second guidewire port until the distal end of the dilatation catheter exits the proximal end of the guiding catheter, or an adapter attached thereto, at which point the portion of the guidewire exposed distal to the dilatation catheter can be manually held in position while the catheter is removed from the proximal end thereof. If the catheter has been used in an over-the-wire mode, the in-place guidewire exits the second arm of the adapter on the proximal end of the catheter shaft. The guidewire is separated from the proximal section of the catheter shaft through the slits provided in the adapter arm and body and the proximal section of the shaft of the dilatation catheter. The separation continues through the slit in the distal section of the dilatation catheter shaft in the manner previously described for the rapid exchange mode. The dilatation catheter is further withdrawn from the patient until the distal end of the dilatation catheter exits the proximal end of the guiding catheter, at which time the exposed portion of the guidewire can be manually held while the dilatation catheter is pulled off the proximal end of the guidewire.

Once the catheter has been removed from the proximal end of the in-place guidewire, the proximal end of the in-place guidewire is inserted into the guidewire port in the distal end of a replacement catheter and then the replacement catheter can be advanced into the patient's vasculature over the in-place guidewire to perform the intravascular procedure. With the catheter of the invention, the proximal end of the guidewire can be directed out of either the second guidewire port in the catheter body or through second guidewire lumen in the proximal section of the catheter shaft and out the second arm of the adapter depending upon the needs of the physician.

The catheter system of the invention also allows for the exchange of an in-place guidewire during an intraluminal procedure while holding the catheter in place so as to maintain access to the intraluminal position. To replace an in-place guidewire, it is removed from the guidewire-receiving inner lumen of the catheter and the patient by merely pulling on its proximal end which extends out of the patient. When the in-place guidewire is removed from the inner lumen of the in-place catheter, the distal end of the in-place catheter is maintained at the desired location within the patient's artery. The replacement guidewire is inserted into the second arm of the adapter and advanced through the guidewire receiving lumen in the proximal and distal sections of the catheter shaft and out the guidewire port in the distal end of the catheter shaft to the desired location within the patient's body lumen. If the in-place guidewire extends out the proximal guidewire port, it may be desirable to have the replacement guidewire inserted into the proximal portion of the guidewire-receiving inner lumen before the in-place guidewire is removed from the distal portion of the inner lumen so that there is little chance of losing access to the location in the body lumen by the accidental movement of the in-place catheter. When the replacement guidewire is advanced through the in-place catheter and properly positioned in a desired location therein, e.g. across a stenosis in a patient's artery which is to be dilated, the catheter may then be advanced over the replacement guidewire to the desired location so as to perform the desired diagnostic or therapeutic treatment therein.

The intravascular catheter of the invention also allows for the removal and reinsertion of a guidewire, for example, when the physician wishes to change the shape of the distal end of a guidewire during a procedure. In this operative modality, the in-place guidewire can be withdrawn in essentially the manner described above, the distal tip thereof reshaped and then be reintroduced into the in-place catheter in essentially the same manner as described above through the adapter into the guidewire receiving lumen.

As will become more apparent from the following detailed description of the invention, the intravascular catheter system of the invention allows for a wide variety of intravascular procedures which were heretofore difficult, if not impossible, to perform with a single catheter system. These and other advantages are described in the following detailed description when taken in conjunction with the accompanying exemplary drawings.

BRIEF DESCRIPTION OF THE DRAWINGS

FIG. 1 is an elevational view, partially in section, of a dilatation catheter which embodies features of the invention.

FIG. 2 is a plan view of the proximal end of the catheter shown in FIG. 1 taken along the lines 2—2.

FIG. 3 is a transverse, cross-sectional view of the catheter shown is FIG. 1 taken along the lines 3—3.

FIG. 4 is a transverse, cross-sectional view of the catheter shown in FIG. 1 taken along the lines 4—4.

FIG. 5 is a plan view of the lower portion of the adapter on catheter shown in FIG. 1 taken along the lines 5—5.

FIG. 6 is a transverse, cross sectional view of the catheter shown in FIG. 1 taken along the lines 6—6.

FIG. 7 is a longitudinal cross-sectional view of a modification of catheter shown in FIG. 1 at the junction between the proximal and distal sections of the catheter.

DETAILED DESCRIPTION OF THE INVENTION

Figure 8:
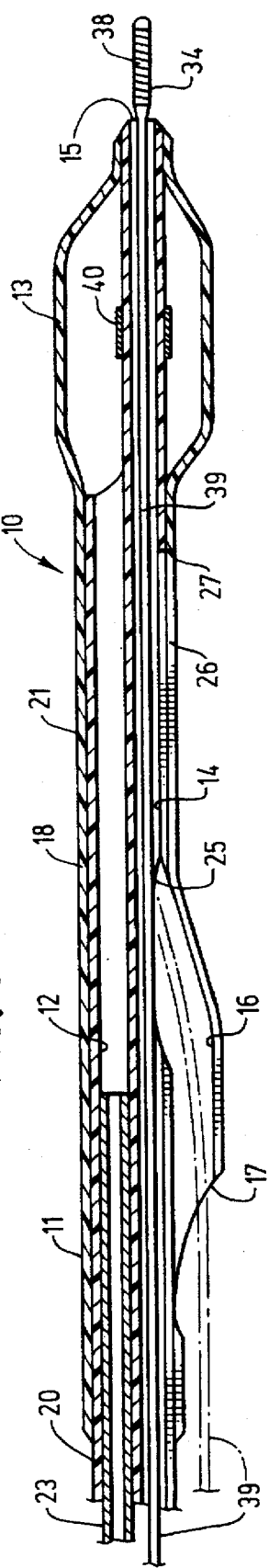
FIG. 8 illustrates an alternate embodiment of the invention in which the inflation lumens and the guidewire lumens of the catheter in both the proximal and distal sections are in-line.

FIGS. 1–6 illustrate a rapid exchange type dilatation catheter 10 embodying features of the invention which allows for the exchange of a guidewire while the catheter remains in place within a patient's arterial system so as to avoid loss of the arterial position. The catheter 10 generally comprises an elongated catheter shaft 11, a first, or guidewire-receiving inner lumen 14 extending therein from the proximal end of the catheter shaft to a guidewire port 15 in the distal end of the catheter shaft a second, or inflation, lumen 12 adapted to direct inflation fluid from the proximal end of the catheter shaft to the interior of an inflatable balloon 13 on a distal portion of the catheter body. A guidewire extension lumen 16 of the guidewire receiving inner lumen 14 extends proximally from the intersection between the extension lumen and the inner lumen 14 to a proximal guidewire port 17 which is offset from the inner lumen 14. Preferably, the most proximal portion of the extension lumen 16 is parallel to the inner lumen 14.

The proximal guidewire port 17 is spaced proximally a short distance from the distal guidewire port 15 in the distal end of the catheter shaft 11 and is preferably at least about 10 cm from the distal end of the catheter body and a substantial distance from the proximal end of the catheter shaft. The proximal guidewire port 17 can be spaced up to about 50 cm from the distal end of the catheter shaft 11.

The distal end of the balloon 13 is sealingly bonded to the distal end of the catheter shaft 11. The proximal end of the balloon 13 may be provided with an elongated waist 18 which forms in part the extension lumen 16 and the proximal guidewire port 17.

As shown best in FIG. 4, the elongated proximal section 20 of the catheter shaft 11 is of a dual lumen construction with the inflation lumen 12 having a circular transverse cross-section and the guidewire receiving lumen 14 having a circular transverse cross-section. As shown in FIG. 5, the distal shaft section 21 is of a dual lumen construction with the both the inflation lumen 12 and the guidewire receiving lumen 14 having circular cross-sections. The inflation lumen 12 terminates at the proximal end of the balloon 13 but a tubular element 22 which defines in part the guidewire receiving lumen 14 extends as part of the shaft 11 to the distal end thereof. The inflation lumen 12 within the proximal section 20 is preferably provided with supporting inner tubular member 23 formed of high strength material such as polyamide, stainless steel or a suitable superelastic Nitinol. The waist 18 of the balloon is secured in a suitable manner to the exterior of the distal section 21 or the shaft 11 and a distal portion of the proximal section 20 of the shaft 11. The waist 18 may be heat shrunk onto the exterior of the shaft 11 or may be heat fused or adhesively bonded to the exterior of the shaft. As indicated the waist 18 forms the guidewire extension lumen 16 and the proximal port 17. The proximal section 20 of the catheter shaft 11 is provided with a proximal slit 24 which extends from the proximal end of the shaft 11 to the opening 25 in the shaft wall where the extension lumen 16 intersects with and is in fluid communication with the main guidewire lumen 14. The distal shaft section 21 is provided with distal slit 26 which extends from the proximal guidewire port 17 to a location 27 proximal to the proximal end of the balloon 13.

Figure 1A:
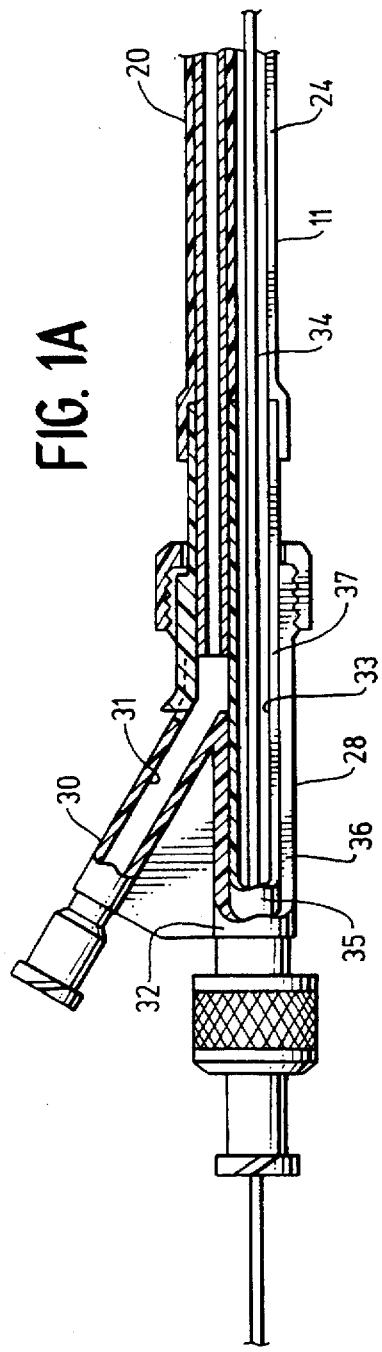
FIG. 1A is an elevational view of an adapter which embodies features of the invention.

As best shown in FIG. 1A, a multi-arm adapter 28, which is provided on the proximal end of the catheter shaft 11, has a second arm 30 with an inner lumen 31 which is adapted to introduce inflation fluid into the inflation lumen 12 and a first arm 32 with an inner lumen 33 which is adapted to receive a guidewire 34 and guide the guidewire into the guidewire receiving lumen 14 within the catheter shaft 11. The proximal end of the catheter shaft 11 is provided with an insert 35 which fits into the interior of the adapter 28 as shown. The insert 35 comprises a tubular section 43 having a distal end 45 and a proximal end 46. The tubular section 43 is disposed within the inner lumen 33 of the first arm 32 of the adapter 28, and defines in part the second inner lumen 31 of the second arm 30. In one embodiment of the invention, the insert 35 has a section 44 having a distal end 47 and a proximal end 48. The insert section 44 extends into the inner lumen 31 of the second arm 30 of the adapter 28 and contains a length of the second inner lumen 31 defined by the insert. The arm 32 of adaptor 28 is modified to include a slit 36 and the insert 35 is provided with a slit 37 both of which are continuous with the slit 24 in the proximal section 20 of the catheter shaft 11. A portion of the insert 35 sealingly connects the inner lumen 31 with the inner inflation lumen 12 within the catheter shaft. The insert 35 may be formed as a separate element and then secured to the proximal end of the catheter shaft 11 or formed as part of the catheter shaft as depicted in FIG. 1.

The inner lumen 14 within the shaft 11 is adapted to slidably receive guidewire 34. The distal end of the guidewire 34 has a coil 38 on the distal end thereof which is shown in FIG. 1 extending out the distal guidewire port 15 in the distal end of the catheter shaft 11 and has an elongated core member 39 which is shown extending through the guidewire lumen 14 and out the arm 32 of the adapter 28 as would be the case when the catheter is utilized in an over-the-wire mode. The elongated core member 39 is shown in phantom within extension lumen 16 and extending out the proximal guidewire port 17 which would be the case when the catheter was used in a rapid exchange mode.

A radiopaque marker 40 is disposed about the tubular element 22 which extends within the interior of the balloon 13 to facilitate the fluoroscopic observation thereof during an intravascular procedure. Another radiopaque marker (not shown) may also be provided on the proximal portion 20 of the catheter body 11 to allow the physician to fluoroscopically determine the location of the proximal guidewire port 17 during an intravascular procedure. Visual markers (not shown) for the brachial and femoral arteries may be provided on the proximal section 20 of the shaft 11 in a conventional fashion.

The catheter system of the invention can be inserted into the patient in a conventional rapid exchange fashion with the guidewire 34 preloaded within the inner lumen 14 in the distal section 21 and extending proximally through the extension lumen 16 and out the proximal guidewire port 17 or it can be inserted in a conventional over-the-wire fashion with the guidewire extending through the entire lumen 14 and out the second arm 32 of the adapter 24. When it becomes desirable or necessary at any time during the intravascular procedure to remove or replace either the catheter 10 or the guidewire 34 either may be removed by pulling on the proximal end thereof which extends out of the patient while the catheter or guidewire which remains within the patient is held in position in order to maintain access to the desired intravascular location about the distal end of the catheter.

If the guidewire 34 is to be removed when in a rapid exchange mode of operation, the catheter 10 is held in place while the guidewire is pulled out of the proximal end of the guiding catheter (not shown) or and adapter thereon. In the over-the-wire mode the guidewire will extend out of the proximal end of the arm 32 of the adapter 28. After the guidewire 34 has been removed from the catheter 10, a replacement guidewire may then be inserted through the end of the arm 32 of the adapter 28 into the inner lumen 14 and advanced therein until the guidewire exits the distal guidewire port 15 in the distal end of the catheter body 11 into the patient's coronary artery. Once the replacement guidewire is properly positioned within the patient's artery, e.g. across a stenosis to be dilated, the dilatation catheter 10 may then be further advanced within the artery, if necessary, over the replacement guidewire to the desired location therein to perform the dilatation or other diagnostic or therapeutic procedure in a conventional manner.

If the catheter 10 is to be removed and the guidewire 34 extends proximally out the arm 32 of the adapter 28, the guidewire and the catheter are separated while the catheter is being withdrawn from the proximal end of the guiding catheter (or adapter thereon) by pulling the guidewire through the slit 36 in the adapter arm 32, the slit 37 in the insert 35 and the slit 24 in the proximal section 20 of the shaft 11 and then slit 26 in the distal section of the catheter shaft 11. When the distal end of the catheter 10 is pulled out of the proximal end of the guiding catheter (or the adapter thereon), the exposed portion of the guidewire 34 distal to the distal end of the catheter 10 may be manually gripped to hold it in place and the catheter 10 can then be removed from the proximal end of the guidewire. If the guidewire 34 exits the proximal port 17 of the catheter, i.e. the catheter is used in the rapid exchange mode, the catheter is withdrawn and separated from the guidewire through the distal slit 26 until a section of the guidewire 34 is exposed distal to the catheter. The rest of the procedure is essentially the same as that previously described.

When the catheter 10 has been removed, the replacement catheter is mounted onto the proximal end of the guidewire by inserting the proximal end of the guidewire through a distal guidewire port in the distal end of the replacement rapid exchange type catheter and advancing the catheter over the guidewire disposed within a guidewire receiving lumen of the replacement catheter until the guidewire exits proximal guidewire port in a rapid exchange fashion. The proximal end of the guidewire is held while the replacement catheter is advanced within the patient in a conventional manner as described in Yock or Horzewski et al. which have been incorporated herein.

The catheter body 11 can be formed by conventional techniques, e.g. extruding, from materials already found useful in intravascular catheters such a polyethylene, polyvinyl chloride, polyesters and composite materials such as described in U.S. Pat. No. 4,981,478 (Evard et al.). The various components of the catheter can be joined by suitable adhesive such as the acrylonitrile based adhesive sold as Loctite™ 405. Heat shrinking may also be employed where appropriate. A venting means may be provided to remove air from the interior of the balloon before the catheter is inserted into the patient such as described in U.S. Pat. No. 4,638,805 (Powell) and U.S. Pat. No. 4,821,722 (Samson et al.) which have been incorporated herein.

The size of the catheter body 11 and the guidewire-receiving inner lumen 14 thereof to a large extent are determined by the size of the guidewires 34 to be employed and the size of the artery or other body lumen through which the catheter must pass. Generally, the diameter of the inner lumen 14 is sufficient to accommodate the guidewire and to allow it to be slidably disposed therein. The diameters of guidewires for coronary use can vary from about 0.006 to about 0.035 inch (0.2–0.89 mm) in diameter, and the inner diameter of the guidewire-receiving inner lumen 14 of the catheter 10 should be about 0.001 to about 0.005 inch (0.025–0.127 mm) larger than the diameter of the guidewire. The catheter body 11 is sufficiently long to extend from outside the proximal end of a guiding catheter, which likewise extends out of the patient, to a stenosis to be treated within the patient's vascular system (or other desired location therein), e.g. from about 100 to about 150 cm when a Seldinger approach through the femoral artery is employed to introduce the catheter 10 into the patient's vasculature. The wall forming the catheter must be of sufficient thickness and strength so that it can be pushed over the guidewire 34 to the desired location within the patient's blood vessel.

FIG. 7 illustrates an enlarged view of an embodiment similar to that shown in FIG. 1 in which a supporting cortically shaped member 41 is provided at the intersection between the main guidewire lumen 14 and the guidewire lumen extension 16. The smaller diameter end of the conically shaped member 41 is positioned in the distal direction. Essentially all of the other elements of the catheter are the same as in the embodiment shown in FIG. 1 and are similarly numbered.

FIG. 8 is an alternative embodiment of the invention wherein the portions of the inflation lumen 12 and the main guidewire receiving 14 in the proximal section 20 of the catheter shaft 11 are in line with the corresponding portions of these lumens in the distal section 21 of the catheter shaft. The guidewire lumen extension 16 is inclined away from the portion of the guidewire lumen 14 in the distal shaft section 21. The portion of the guidewire lumen extension 16 adjacent to the proximal guidewire port 17 is off-set and generally parallel to the main guidewire lumen 14 in the proximal shaft section 20. A truncated conical support section 41 is provided in the intersection between the main guidewire lumen 14 and the guidewire lumen extension 16 as in FIG. 7.

While the invention has been described herein in terms of certain presently preferred embodiments directed to balloon dilatation catheters for use in coronary angioplasty procedures, those skilled in the art will recognize that the catheter of the invention may be used in a variety of body lumens. For example, the invention can be utilized in a wide variety of diagnostic and therapeutic intravascular catheters. Additionally, the catheter body may be of concentric construction rather than the dual lumen construction shown herein. Other modifications and improvements may be made to the invention without departing from the scope thereof.

What is claimed is:

1. An intravascular catheter comprising:
   a) an elongated catheter shaft having proximal and distal ends, a guidewire port in the distal end, a first inner lumen extending from the proximal end to the port in the distal end of the catheter shaft, a second inner lumen extending from the proximal end to a location spaced proximally from the distal end of the catheter shaft, a longitudinally extending slit in a wall portion of a proximal section of the catheter shaft which is in communication with the first inner lumen and which extends to the proximal end of the catheter shaft; and
   b) a multi-arm adapter secured to the proximal end of the catheter shaft having a first arm with an inner lumen which is in communication with first inner lumen extending within the proximal end of the catheter shaft and which has a slit therein which is continuous with the slit provided in a proximal section of the catheter shaft to which the adapter is secured, a second arm with a second inner lumen which is in fluid communication with the second inner lumen of the catheter shaft, an insert disposed within the adapter having a tubular section disposed within the inner lumen of the first arm and provided with a slit therein coextensive at least in part with the slit in the first arm and defining in part the second inner lumen of the second arm.

2. The intravascular catheter of claim 1 wherein the insert has a section which extends into the inner lumen of the second arm and contains a length of the second inner lumen defined by the insert.

3. A multi-arm adapter for a proximal end of a balloon dilatation catheter having an inflation lumen and a guidewire lumen extending to the proximal end of the catheter, the adapter comprising
   a) a first arm having a proximal end and a distal end, an inner lumen which is to be in fluid communication with the guidewire lumen of the catheter and a slit extending from the proximal end to the distal end of the first arm of the adapter;
   b) a second arm at an angle with respect to the first arm having a second inner lumen which is to be in fluid communication with the inflation lumen of the balloon dilatation catheter; and
   c) a flexible insert disposed within the interior of the adapter having a tubular extension extending within the first arm of the adapter with a slit in alignment with the slit in the first arm, and defining in part the second inner lumen of the second arm.

4. The multi-arm adapter of claim 3 wherein the flexible insert has a section which extends into the inner lumen of the second arm and contains a length of the second inner lumen defined by the insert.

5. A balloon dilatation catheter comprising:
   a) an elongated catheter shaft having proximal and distal ends,
      a guidewire pod in the distal end,
      an inflation lumen extending from the proximal end of the catheter shaft to a location spaced proximally from the distal end of the catheter shaft,
      a guidewire receiving lumen
      a longitudinally extending slit in a wall portion of a proximal section of the catheter shaft which is in communication with the guidewire lumen and which extends to the proximal end of the catheter shaft, and
      a dilatation balloon on a distal section of the catheter shaft having an interior in fluid communication with the inflation lumen; and
   b) an multi-arm adapter secured to the proximal end of catheter shaft having
      a first arm with an inner lumen which is in communication with the guidewire receiving inner lumen extending within the catheter shaft and with a longitudinally extending slit therein which is continuous with the longitudinally extending slit provided in the proximal section of the catheter shaft,
      a second arm with an inner lumen which is in communication with the inflation lumen in the catheter shaft, and
      an insert disposed within the adapter having a tubular section disposed within the inner lumen of the first arm and a section disposed within the inner lumen of the second arm, with the tubular section having a longitudinally extending slit coextensive at least in part with the longitudinally extending slit in the first arm and defining in part the second inner lumen of the second arm, and with the section containing a length of the second inner lumen defined by the insert.

* * * * *